US007815936B2

(12) United States Patent
Hasenzahl et al.

(10) Patent No.: US 7,815,936 B2
(45) Date of Patent: Oct. 19, 2010

(54) USE OF GRANULAR MATERIALS BASED ON PYROGENICALLY PRODUCED SILICON DIOXIDE IN PHARMACEUTICAL COMPOSITIONS

(75) Inventors: Steffen Hasenzahl, Hanau (DE); Jürgen Meyer, Stockstadt (DE); Jürgen Heym, Hörstein (DE)

(73) Assignee: Evonik Degussa GmbH, Essen (DE)

( * ) Notice: Subject to any disclaimer, the term of this patent is extended or adjusted under 35 U.S.C. 154(b) by 527 days.

(21) Appl. No.: 10/281,223

(22) Filed: Oct. 28, 2002

(65) Prior Publication Data
US 2004/0022844 A1    Feb. 5, 2004

(30) Foreign Application Priority Data
Oct. 30, 2001    (DE)    ............... 101 53 078

(51) Int. Cl.
*A61K 9/48* (2006.01)
*A61K 9/20* (2006.01)
(52) U.S. Cl. ............... 424/452; 424/465; 424/724
(58) Field of Classification Search ............... 424/465, 424/452
See application file for complete search history.

(56) References Cited

U.S. PATENT DOCUMENTS

| 3,946,110 | A | * | 3/1976 | Hill ............... 514/161 |
| 4,940,588 | A | * | 7/1990 | Sparks et al. ............... 424/490 |
| 4,980,487 | A | * | 12/1990 | Thies et al. ............... 549/396 |
| 5,191,114 | A | * | 3/1993 | Chen ............... 562/496 |
| 5,585,115 | A | | 12/1996 | Sherwood et al. |
| 5,762,912 | A | * | 6/1998 | Eteve ............... 424/59 |
| 5,776,240 | A | * | 7/1998 | Deller et al. ............... 106/482 |
| 5,879,706 | A | * | 3/1999 | Carter et al. ............... 424/464 |
| 6,083,491 | A | * | 7/2000 | Mellul et al. ............... 424/63 |
| 6,103,219 | A | * | 8/2000 | Sherwood et al. ............... 424/49 |
| 6,217,909 | B1 | | 4/2001 | Sherwood et al. |
| 6,607,748 | B1 | * | 8/2003 | Lenaerts et al. ............... 424/464 |

| 2001/0001664 | A1 | 5/2001 | Sherwood et al. |

FOREIGN PATENT DOCUMENTS

| EP | 0 274 845 A1 | 7/1988 |
| EP | 0 725 037 B1 | 8/1996 |
| JP | 02-044023 A | 2/1990 |
| JP | 2001518500 T | 10/2001 |
| WO | WO 95/14904 A2 | 6/1995 |
| WO | WO 95/14904 A3 | 6/1995 |
| WO | 99/17766 A1 | 4/1999 |
| WO | 00/27362 A1 | 5/2000 |

OTHER PUBLICATIONS

Gustav Fischer and Stuttgart Jena; Bauer, Fromming, Fuhrer, Pharmaceutical Technology; Lubeck Ulm XP002225023; ISBN: 3-437-25630-0; 1997; pp. 305 col. 2, paragraoh 5 and p. 306 col. 1, paragraph 1.

Von H. Rupprecht et al., "Letters to the Editors/Wissenschaftliche Kurzberichte", Colloid & Polymer Sci., vol. 252, pp. 415-416, (1974).

D. C. Monkhouse et al., "Use of Adsorbents in Enhancement of Drug Dissolution I", Journal of Pharmaceutical Sciences, vol. 61(9)1430-1435, (1972).

Von H. Flasch et al., "Erhöhte Bioverfügbarkeit von Digoxin aus Kieselsäure-Matrix-Zubereitungen", Arneim-Forschung/Drug. Res., vol. 28(1):326-330, (1978).

A. Y. Gore et al., "Surface Chemistry of Colloidal Silica and a Possible Application to Stabilize Aspirin in Solid Matrixes", Journal of Pharmaceutical Sciences, vol. 68(2):197-202, American Pharmaceutical Association, (1979).

Technical Information, No. 1237, "Aerosil 200 Pharma- A Versatile Excipient for the Pharmaceutical Industry", Degussa, pp. 1-15, Sep. 2001.

* cited by examiner

*Primary Examiner*—Jake M. Vu
(74) *Attorney, Agent, or Firm*—Smith, Gambrell & Russell, LLP

(57) ABSTRACT

The use of granular materials based on pyrogenically produced silicon dioxide in pharmaceutical compositions, the pharmaceutical compositions per se, as well as an adsorbate consisting of the granular material and at least one further substance selected from pharmaceutical active constituents and auxiliary substances, and the production of such adsorbates, are described.

8 Claims, No Drawings

USE OF GRANULAR MATERIALS BASED ON PYROGENICALLY PRODUCED SILICON DIOXIDE IN PHARMACEUTICAL COMPOSITIONS

The present invention relates to the use of granular materials of pyrogenic silicic acid in pharmaceutical compositions. The granular materials are used in this connection in particular as carriers of pharmaceutical active constituents and/or auxiliary substances.

Medicament compositions contain in addition to the actual active constituent a number of further constituents, the so-called auxiliary substances or adjuvants, in order to convert the active constituent into suitable preparations that are effective at the desired point of use. A problem with many medicaments is their low solubility in water, resulting in a poor bioavailability and thereby often in an inadequate efficacy. In order to increase their solubility they may be adsorbed on suitable matrices having a high surface area. Pyrogenic silicic acids for example are suitable for this purpose, and are characterised by a high purity and inert behaviour compared to other active constituents and auxiliary substances. They also adsorb numerous medicaments reversibly. Pyrogenic silicic acids correspond to the pharmacopoeia monographs for highly dispersed silicon dioxide (for example European Pharmocopoeia Monograph No. 437) and may be used without any restrictions in pharmaceutical products.

It is known that for example by applying ethinyl oestradiol to pyrogenic silicic acid, its release rate can be significantly improved (product leaflet "Pigments" No. 19, Degussa AG). For example, the sorbate of 5.2 mg of this active constituent on 100 mg of pyrogenic silicic acid (AEROSIL 200, Degussa AG) on contact with water releases so much active constituent that a supersaturated solution is formed. An equivalent amount of the pure active constituent reaches the saturation equilibrium value of 1.1 mg/100 ml only after shaking over several days.

Numerous further AEROSIL 200 sorbates exhibit an improved active constituent release behaviour, for example those of griseofulvin (H. Rupprecht, M. J. Biersack, G. Kindl, Koll.-ZZ. Polym. 252 (1974) 415), indomethacin, aspirin, sulfaethidole, reserpine, chloramphenicol, oxolinic acid, probucol and hydrochlorothiazide (D. C. Monkhouse, J. L. Lach, J. Pharm. Sci., 57 (1968) 2143). Also, digitoxin-silicic acid matrices are characterised by an increased bioavailability compared to the pure active constituent (H. Flasch, B. Asmussen, N. Heinz, Arzneim.-Forschung/Drug. Res. 28 (1978) 326).

In addition to the improvement in the bioavailability of sparingly soluble medicaments, carrier materials such as pyrogenic silicic acid may also be used in order to protect active constituents against environmental influences such as for example atmospheric oxygen, light or moisture and thereby stabilise them. For example, A. Y Gore et al. in J. Pharm. Sci. 68 (1979) 197 describe the stabilisation of acetylsalicylic acid against hydrolysis by means of highly dispersed silicic acid. A targeted or delayed release of active constituent may also be achieved by adsorption on a carrier.

Pyrogenic silicic acids act however not only as carriers for active constituents, but may also be used in order to convert liquid or pasty active constituents into flowable powders. In this connection the active constituents are stored in the void volumes of the pyrogenic silicic acid aggregates. The powders that are thereby produced may be processed further into widely differing medicament forms, such as for example tablets, capsules, ointments, creams or suppositories (product leaflet "Pigments" No. 49, Degussa AG).

Pyrogenic silicic acid may also be used as an antiblocking agent, disintegration accelerator, suspension stabiliser and consistency regulator in tablets, capsules, suppositories, ointments and aerosols. Further possible uses of pyrogenic silicic acid as a pharmaceutical auxiliary substance are described in Technichal Information Leaflet No. 1237 "AEROSIL 200 Pharma—A versatile excipient for the pharmaceutical industry", Degussa AG.

However, the use of pyrogenic silicic acids employed hitherto in medicament preparations does have some disadvantages. For example, a considerable amount of dust is formed during processing, which necessitates a complicated and expensive handling procedure. Furthermore available pyrogenic silicic acid has a relatively low bulk density and tamped density and is therefore bulky to transport and store. Also, available adsorbates of pyrogenic silicic acid and a medicament often have an insufficient flowability and an unknown active constituent release behaviour on account of a very broad grain size distribution dependent on their processing.

The replacement of pyrogenic silicic acid by precipitated silicic acids or silica gels is possible only to a limited extent since their purity is often not sufficient. In addition to a relatively high salt and water content contamination by germs cannot be reliably ruled out since these products are generally produced at temperatures below 100° C.

The object of the present invention is accordingly to provide an auxiliary substance for use in pharmaceutical compositions that does not exhibit the aforementioned disadvantages and also satisfies the stringent requirements of the pharmaceutical industry as regards purity and product safety.

This object is achieved by the use of a granular material based on pyrogenically produced silicon dioxide in a pharmaceutical composition. The present invention also provides a pharmaceutical composition that contains a granular material based on pyrogenically produced silicon dioxide and at least one pharmaceutical active constituent. In addition the present invention is directed to an adsorbate consisting of a granular material based on pyrogenically produced silicon dioxide and at least one further substance selected from pharmaceutical active constituents and auxiliary substances, and to the production of such adsorbates.

Preferably the granular material based on pyrogenically produced silicon dioxide has a mean grain diameter of 10 to 120 μm and a BET surface of 40 to 400 m²/g (determination according to DIN 66 131 with nitrogen).

Preferably the silicon dioxide granular material exhibits the following physicochemical characteristic data, which are determined as described in EP PS 0 725 037:

| | |
|---|---|
| Pore volume: | 0.5 to 2.5 ml/g |
| Pore size distribution: | less than 5% of the overall pore volume has a pore diameter of less than 5 nm, the remainder being mesopores and macropores |
| pH value: | 3.6 to 8.5 |
| Tamped density: | 220 to 700 g/l. |

A suitable granular material for the use according to the invention and its production is described for example in EP OS 0 727 037.

Preferably the granular material may exhibit mesopores and macropores, the volume of the mesopores accounting for 10 to 80% of the total volume. The particle size distribution of the granular material is preferably 80 vol. % greater than 8 μm and 80 vol. % less than 96 μm. The proportion of pores smaller than 5 μm may in a preferred embodiment of the invention be at most 5% referred to the total pore volume.

The granular material used according to the invention may be produced for example by dispersing in water pyrogenically produced silicon dioxide, preferably silicon dioxide produced by means of flame hydrolysis from silicon tetrachloride, following which the granular material is spray dried and optionally heat treated at a temperature of 150° to 1,100° C. for a period of 1 to 8 hours.

The dispersion in water preferably has a concentration of silicon dioxide of 5 to 25 wt. %, more preferably 5 to about 19.9 wt. %. The spray drying may be carried out at a temperature of 200° to 600° C., in which connection rotarydisc atomisers or nozzle atomisers may be used. The heat treatment of the granular material may be carried out under fixed bed conditions, for example in chamber furnaces, as well as under fluidised bed conditions, for example rotary tubular dryers.

The pyrogenic silicon dioxide serving as starting material is produced by feeding a volatile silicon compound through a nozzle into a detonating gas flame of hydrogen and air. Silicon tetrachloride is used in most cases. This substance hydrolyses under the influence of the water produced in the detonating gas reaction, to form silicon dioxide and hydrochloric acid. After leaving the flame the silicon dioxide enters a so-called coagulation zone in which the silicon dioxide primary particles and primary aggregates agglomerate. The product present as a form of aerosol in this stage is separated from the gaseous accompanying substances in cyclones and is then post-treated with moist hot air. The residual hydrochloric acid content can be reduced to below 0.025% by this process.

The granular materials based on pyrogenically produced silicon dioxide may also be silanised. The carbon content of the granular material is then preferably 0.3 to 15.0 wt. %. Halogenated silantes, alkoxysilanes, silazanes and/or siloxanes may be used for the silanisation.

The following substances in particular may be used as halogenated silanes:

halogenated organosilanes of the type $X_3Si(C_nH_{2n+1})$ X=Cl, Br
   n=1-20 halogenated organosilanes of the type $X_2(R')Si(C_nH_{2n+1})$
   X=Cl, Br
   R'=Alkyl
   n=1-20 halogenated organosilanes of the type $X(R')_2Si(C_nH_{2n+1})$
   X=Cl, Br
   R'=Alkyl
   n=1-20 halogenated organosilanes of the type $X_3Si(CH_2)_m$—R'
   X=Cl, Br
   m=0.1-20
   R'=Alkyl, aryl (e.g. —$C_6H_5$)
     —$C_4F_9$, —$OCF_2$—CHF—$CF_3$, —$C_6F_{13}$, —O—$CF_2$—$CHF_2$
     —$NH_2$, —$N_3$, —SCN, —CH=$CH_2$,
     —$OOC(CH_3)C=CH_2$
     —$OCH_2$—CH(O)$CH_2$

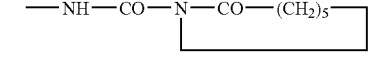

—NH—COO—$CH_3$,   —NH—COO—$CH_2$—$CH_3$,
   —NH—$(CH_2)_3$Si(OR)$_3$
   —$S_x$—$(CH_2)_3$Si(OR)$_3$ halogenated organosilanes of the type $(R)X_2Si(CH_2)_m$—R'
   X=Cl, Br
   R=Alkyl
   m=0.1-20
   R'=Alkyl, aryl (e.g. —$C_6H_5$)
     —$C_4F_9$, —$OCF_2$—CHF—$CF_3$, —$C_6F_{13}$, —O—$CF_2$—$CHF_2$
     —$NH_2$, —$N_3$, —SCN, —CH=$CH_2$,
     —$OOC(CH_3)C=CH_2$
     —$OCH_2$—CH(O)$CH_2$

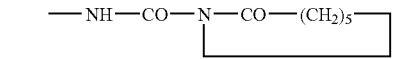

—NH—COO—$CH_3$,   —NH—COO—$CH_2$—$CH_3$,
   —NH—$(CH_2)_3$Si(OR)$_3$
   —$S_x$—$(CH_2)_3$Si(OR)$_3$ halogenated organosilanes of the type $(R)_2X Si(CH_2)_m$—R'
   X=Cl, Br
   R=Alkyl
   m=0.1-20
   R'=Alkyl, aryl (e.g. —$C_6H_5$)
     —$C_4F_9$, —$OCF_2$—CHF—$CF_3$, —$C_6F_{13}$, —O—$CF_2$—$CHF_2$
     —$NH_2$, —$N_3$, —SCN, —CH=$CH_2$,
     —$OOC(CH_3)C=CH_2$
     —$OCH_2$—CH(O)$CH_2$

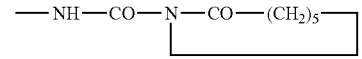

—NH—COO—$CH_3$,   —NH—COO—$CH_2$—$CH_3$,
   —NH—$(CH_2)_3$Si(OR)$_3$
   —$S_x$—$(CH_2)_3$Si(OR)$_3$

The following substances in particular may be used as alkoxysilanes:

organosilanes of the type $(RO)_3Si(C_nH_{2n+1})$
   R=Alkyl
   n=1-20 organosilanes of the type $R'_x(RO)_ySi(C_nH_{2n+1})$
   R=Alkyl
   R'=Alkyl
   n=1-20
   x+y=3
   x=1.2
   y=1.2 organosilanes of the type $(RO)_3Si(CH_2)_m$—R'
   R=Alkyl
   m=0.1-20
   R'=Alkyl, aryl (e.g. —$C_6H_5$)
     —$C_4F_9$, $OCF_2$—CHF—$CF_3$, —$C_6F_{13}$, —O—$CF_2$—$CHF_2$
     —$NH_2$, —$N_3$, —SCN, —CH=$CH_2$,
     —$OOC(CH_3)C=CH_2$
     —$OCH_2$—CH(O)$CH_2$

—NH—COO—$CH_3$,   —NH—COO—$CH_2$—$CH_3$,
   —NH—$(CH_2)_3$Si(OR)$_3$
   —$S_x$—$(CH_2)_3$Si(OR)$_3$ organosilanes of the type $(R'')_x(RO)_ySi(CH_2)_m$—R'

R″=Alkyl
x+y=2
x=1.2
y=1.2
R′=Alkyl, aryl (e.g. —C$_6$H$_5$)
—C$_4$F$_9$, —OCF$_2$—CHF—CF$_3$, —C$_6$F$_{13}$, —O—CF$_2$—CHF$_2$
—NH$_2$, —N$_3$, —SCN, —CH=CH$_2$,
—OOC(CH$_3$)C=CH$_2$
—OCH$_2$—CH(O)CH$_2$

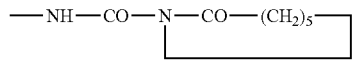

—NH—COO—CH$_3$, —NH—COO—CH$_2$—CH$_3$,
—NH—(CH$_2$)$_3$Si(OR)$_3$
—S$_x$—(CH$_2$)$_3$Si(OR)$_3$

The silane Si 108 [(CH$_3$O)$_3$—Si—C$_8$H$_{17}$] trimethoxyoctylsilane may preferably be used as silanisation agent.

The following substances in particular may be used as silazanes:
Silazanes of the type:

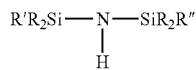

R=Alkyl
R′=Alkyl, vinyl as well as for example hexamethyldisilazane.

The following substances in particular may be used as siloxanes:
cyclic polysiloxanes of the type D 3, D 4, D 5, e.g. octamethylcyclotetrasiloxane=D 4

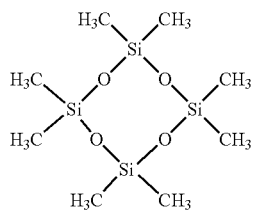

polysiloxanes and/or silicone oils of the type:

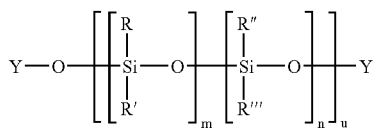

R=Alkyl, aryl, (CH$_2$)$_n$—NH$_2$, H
R′=Alkyl, aryl, (CH$_2$)$_n$—NH$_2$, H
R″=Alkyl, aryl, (CH$_2$)$_n$—NH$_2$, H
R‴=Alkyl, aryl, (CH$_2$)$_n$—NH$_2$, H
Y=CH$_3$, H, C$_n$H$_{2n+1}$ where n=1-20
Y=Si(CH$_3$)$_3$, Si(CH$_3$)$_2$H
Si(CH$_3$)$_2$OH, Si(CH$_3$)$_2$(OCH$_3$)
Si(CH$_3$)$_2$(C$_n$H$_{2n+1}$) where n=1-20
m=0, 1, 2, 3, … ∞
n=0, 1, 2, 3, … ∞
u=0, 1, 2, 3, … ∞

The silanisation may be carried out by spraying the granular material with the silanisation agent, which may optionally be dissolved in an organic solvent, for example ethanol, and then thermally treating the mixture at a temperature of 105° to 400° C. for a period of 1 to 6 hours.

An alternative method of silanising the granular materials involves treating the granular material with the silanisation agent in vapour form and then thermally treating the mixture at a temperature of 200° to 800° C. for a period of 0.5 to 6 hours. The thermal treatment may be carried out under a protective gas, such as for example nitrogen.

The silanisation may be carried out continuously or batchwise in heatable mixers and dryers with spray devices. Suitable types of apparatus include for example ploughshare mixers, plate dryers, fluidised-bed dryers or turbulent-layer dryers.

The physicochemical parameters of the granular materials, such as the specific surface, grain size distribution, pore volume, tamped density and silanol group concentration, pore distribution and pH value may be altered within the specified limits by varying the starting substances, spraying conditions, heat treatment and silanisation.

The granular materials of pyrogenic silicon dioxide may be used according to the invention in any suitable solid, semi-solid or liquid medicament forms, preferably for oral and/or topical applications, for example in suspensions, emulsions, aerosols, ointments, creams, gels, pastes, suppositories, sticks, powders, topical powders, granules, tablets, pastilles, sugar-coated pills, film-coated tablets, hard gelatin capsules, soft gelatin capsules, extrudates, microcapsules or microspheres. Particularly preferred are solid medicament forms such as for example powders, granules, tablets and capsules.

The expression "pharmaceutical composition" also covers within the scope of the present invention precursors and intermediates used for the production of granules, tablets, capsules, suspensions, dry ointments and dry drops. Such precursors and intermediates may for example also be in the form of a powder, granular material or extrudate.

Methods for the production of solid, semi-solid and liquid medicament forms are known and are described in numerous publications and textbooks relating to pharmaceutical technology, cf. for example K. H. Bauer, K.-H. Frömming, C. Fuhrer, Lehrbuch der pharmazeutischen Technologie, 6$^{th}$ Edition, Wissenschaftliche Verlagsgesellschaft mbH Stuttgart 1999.

The silicon dioxide granular material may be used in combination with any arbitrary pharmaceutical active constituent. The following may be mentioned by way of example:

α-proteinase inhibitor, abacavir, abciximab, acarbose, acetylsalicylic acid, acyclovir, adenosine, albuterol, aldesleukin, alendronate, alfuzosin, alosetrone, alprazolam, alteplase, ambroxol, amifostine, amiodarone, amisulprid, amlodipine, amoxicillin, amphetamine, amphotericin, ampicillin, amprenavir, anagrelide, anastrozole, ancrod, anti-haemophilia factor, aprotinin, atenolol, atorvastatin, atropine, azelastine, azithromycin, azulene, barnidipin, beclomethasone, benazepril, benserazide, beraprost, betamethasone, betaxolol, bezafibrate, bicalutamide, bisabolol, bisoprolol, botulinum toxin, brimonidine, bromazepam, bromocriptine, budesonide, bupivacaine, bupropion, buspirone, butorphanol, cabergoline, calcipotriene, calcitonin, calcitriol, camphor, candesartan, candesartan cilexetil, captopril, carbamazepine, carbidopa, carboplatin, carvedilol, cefaclor, cefadroxil, cefaxitin, cefazolin, cefdinir, cefepime, cefixime, cefmetazole, cefoperazone, cefotiam, cefoxopran, cefpodoxime, cefprozil, ceftazidime, ceftibuten, ceftriaxone, cefuroxime, celecoxib, celiprolol, cephalexin, cerivastatin, cetirizine, chloramphenicol, cilastatin, cilazapril, cimetidine, ciprofibrate, ciprofloxacin, cisapride, cisplatin, citalopram, clarithromycin, clavulanic acid, clindamycin, clomipramine, clonazepam, clonidine, clopidogrel, clotrimazole, clozapine, cromolyn, cyclophosphamide, cyclosporine, cyproterone, dalteparin, deferoxamine, desogestrel, dextroamphetamine, diazepam, diclofenac, didanosine, digitoxin, digoxin, dihydroergotamine, diltiazem, diphtheria protein, diphtheria toxoide, divalproex, dobutamine, docetaxel, dolasetron, donepezil, dornase-α, dorzolamide, doxazosin, doxifluridin, doxorubicin, dydrogesterone, ecabet, efavirenz, enalapril, enoxaparin, eperisone, epinastin, epirubicin, eptifibatide, erythropoietin-α, erythropoietin-β, etanercept, ethinyl oestradiol, etodolac, etoposide, factor VIII, famciclovir, famotidine, faropeneme, felodipine, fenofibrate, fenoldopam, fentanyl, fexofenadin, filgrastim, finasteride, flomoxef, fluconazole, fludarabine, flunisolide, flunitrazepam, fluoxetine, flutamide, fluticasone, fluvastatin, fluvoxamine, follitropin-α, follitropin-β, formoterol, fosinopril, furosemide, gabapentin, gadodiamide, ganciclovir, gatifloxacin, gemcitabine, gestoden, glatiramer, glibenclamide, glimepiride, glipizide, glyburide, goserelin, granisetron, griseofulvin, hepatitis B antigen, hyaluronic acid, hycosin, hydrochlorothiazide, hydrocodone, hydrocortisone, hydromorphone, hydroxychloroquine, hylan G-F 20, ibuprofen, ifosfamide, imidapril, imiglucerase, imipenem, immunoglobulin, indinavir, indomethacin, infliximab, insulin, insulin human, insulin Lispro, insulin aspart, interferon β, interferon α, iodine 125, iodixanol, iohexol, iomeprol, iopromid, ioversol, ioxoprolen, ipratropium, ipriflavone, irbesartan, irinotecan, isosorbide, isotretinoin, isradipine, itraconazole, potassium chlorazepate, potassium chloride, ketorolac, ketotifen, whooping cough vaccine, coagulation factor IX, lamivudine, lamotrigine, lansoprazole, latanoprost, leflunomide, lenograstim, letrozole, leuprolide, levodopa, levofloxacin, levonorgestrel, levothyroxine, lidocaine, linezolid, lisinopril, lopamidol, loracarbef, loratadine, lorazepam, losartan, lovastatin, lysineacetylsalicylic acid, manidipin, mecobalamin, medroxyprogesterone, megestrol, meloxicam, menatetrenone, meningococcus vaccine, menotropine, meropenem, mesalamine, metaxalone, metformin, methylphenidate, methylprednisolone, metoprolol, midazolam, milrinone, minocycline, mirtazapine, misoprostol, mitoxantrone, moclobemid, modafinil, mometasone, montelukast, morniflumat, morphine, moxifloxacin, mycophenolate, nabumetone, nadroparin, naproxen, naratriptan, nefazodone, nelfinavir, nevirapine, niacin, nicardipine, nicergoline, nifedipine, nilutamide, nilvadipine, nimodipine, nitroglycerin, nizatidine, norethindrone, norfloxacin, octreotide, olanzapine, omeprazole, ondansetron, orlistate, oseltamivir, oestradiol, oestrogens, oxaliplatin, oxaprozin, oxolinic acid, oxybutynin, paclitaxel, palivizumab, pamidronate, pancrelipase, panipenem, pantoprazol, paracetamol, paroxetine, pentoxifylline, pergolide, phenytoin, pioglitazon, piperacillin, piroxicam, pramipexole, pravastatin, prazosin, probucol, progesterone, propafenone, propofol, propoxyphene, prostaglandin, quetiapine, quinapril, rabeprazol, raloxifene, ramipril, ranitidine, repaglinide, reserpine, ribavirin, riluzole, risperidone, ritonavir, rituximab, rivastigmin, rizatriptan, rofecoxib, ropinirol, rosiglitazone, salmeterol, saquinavir, sargramostim, serrapeptase, sertraline, sevelamer, sibutramin, sildenafil, simvastatin, somatropine, sotalol, spironolactone, stavudin, sulbactam, sulfaethidole, sulfamethoxazole, sulfasalazin, sulpirid, sumatriptan, tacrolimus, tamoxifen, tamsulosin, tazobactam, teicoplanin, temocapril, temozolomid, tenecteplase, tenoxicam, teprenon, terazosin, terbinafine, terbutaline, tetanus toxoid, tetrabenazine, tetrazepam, thymol, tiagabine, tibolon, ticarcillin, ticlopidine, timolol, tirofiban, tizanidine, tobramycin, tocopheryl nicotinate, tolterodine, topiramate, topotecan, torasemid, tramadol, trandolapril, trastuzumab, triamcinolone, triazolam, trimebutin, trimethoprim, troglitazone, tropisetrone, tulobuterol, unoproston, urofollitropine, valacyclovir, valproic acid, valsartan, vancomycin, venlafaxine, verapamil, verteporfin, vigabatrin, vinorelbine, vinpocetine, voglibose, warfarin, zafirlukast, zaleplon, zanamivir, zidovudine, zolmitriptan, zolpidem, zopiclone and their derivatives. Pharmaceutical active constituents are however also understood to include other substances such as vitamins, provitamins, essential fatty acids, extracts of plant and animal origin and oils of plant and animal origin.

Further constituents of the pharmaceutical compositions may include conventional auxiliary substances such as for example antioxidants, binders, emulsifiers, colouring agents, film-forming agents, fillers, odoriferous substances, flavouring substances, gel-forming agents, preservatives, solvents, oils, powder bases, ointment bases, acids and salts for the formulation, replenishment and production of pharmaceutical compositions, lubricants, release agents, suppository bases, suspension stabilisers, sweetening agents, effervescent gases, emollients and sugar substitutes.

Plant medicament preparations and homeopathic preparations are also included among the pharmaceutical compositions in which the silicon dioxide granular materials may be used.

The pharmaceutical compositions according to the invention may also include so-called retard and depot medicament forms with controlled release of active constituent. Moreover the pharmaceutical compositions according to the invention may also be part of therapeutic systems such as for example therapeutic systems for topical application and transdermal therapeutic systems.

In a preferred embodiment the silicon dioxide granular material based on pyrogenic silicic acid serves as a carrier for pharmaceutical active constituents and/or auxiliary substances. The present invention is accordingly also directed to an adsorbate of the aforedescribed silicon dioxide granular material and at least one of these substances.

The expression "adsorbate" as used in the present specification covers not only the adsorption of a substance on the surface of the silicon dioxide, but also in the pores, as well as the "incorporation" in the void volumes. The term "adsorbate" may also mean that silicon dioxide granular material or fragments thereof coat solids particles or liquid droplets of the material. In the latter case the forces of attraction between the particles and/or droplets are reduced and for example the flow behaviour is improved and/or the coalescence of droplets is prevented.

In principle the silicon dioxide granular material may act as a carrier for any suitable pharmaceutical active constituent or auxiliary substance; preferred however are adsorbates containing the aforementioned active constituents and auxiliary substances and/or their mixtures. of the pharmaceutical auxiliary substances, there are preferably adsorbed on the silicon dioxide granular material odoriferous substances, flavouring agents or colouring agents. The odoriferous substances and flavouring agents may be of natural, i.e. plant or animal origin, as well as synthetic, i.e. fully synthetic or semi-synthetic origin.

Examples of plant odoriferous substances include ethereal oils and resinoids. Examples of animal odoriferous substances that may be mentioned include musk, civet, castoreum and ambergris. The fully synthetic odoriferous substances include those that have an odoriferous prototype in nature, as well as pure fantasy compositions. Semi-synthetic odoriferous substances are understood to be those that can be isolated from natural fragrances and then chemically converted.

Also, the colouring agents may be natural or synthetic colouring agents, and organic or inorganic compounds.

Granular materials formed from pyrogenic silicic acid are suitable in particular as carriers for substances:

- whose release behaviour is improved by application to a high surface area carrier substance, for example in the case of sparingly water-soluble substances;
- whose release behaviour is too quick, for example in the case of retard formulations;
- that are liquid or pasty and are therefore e.g. difficult to meter and/or handle;
- that can be processed only with difficulty, for example as a result of too low a melting point;
- whose flow behaviour is insufficient for further processing, for example for producing tablets and capsules;
- that are readily volatile;
- that are sensitive to external conditions such as for example atmospheric oxygen, light, moisture, acids (gastric juice) or bases (intestinal fluid).

Numerous active constituents can be stabilised in this way, such as for example acetylsalicylic acid; atropine; azulene; bisabolol; camphor; chloramphenicol; hydrocortisone and its derivatives, such as for example hydrocortisone-17-valerate, prostaglandins; thymol; (pro)vitamins and their derivatives, such as for example vitamin A and E; unsaturated fatty acids, specifically essential fatty acids such as for example gamma-linolenic acid, oleic acid, eicosapentenoic acid and docosahexenoic acid; extracts of animal and plant origin and oils of animal and plant origin, such as for example fish oils, evening primrose oil, borage oil, currant seed oil and cod liver oil.

Sparingly soluble substances whose release behaviour can be improved by application to the granular materials formed from pyrogenic silicic acid include for example indomethacin, sulfaethidole, reserpine, griseofulvin, probucol and oxolinic acid. Also, the release behaviour of per se readily soluble substances such as for example hydrochlorothiazide, chloramphenicol and acetylsalicylic acid can be improved further in this way.

An example of an active constituent that is difficult to process or cannot be processed at all by conventional methods is ibuprofen, above all S-ibuprofen, which has a melting point of only 52° C. On account of the low melting point granulation processes apart from as an adsorbate according to the invention are hardly feasible. Moreover substances that for example sinter during the tabletting form preferred adsorbates within the context of the present invention with the silicon dioxide granular material.

The quantitative ratio of substance to silicon dioxide granular material in the adsorbate may be chosen as desired depending on the properties of the substance and the requirements that the end product has to meet. However, preferably 0.001 to 200 g of substance, particularly preferably 10 to 150 g of substance, are used per 100 g of silicon dioxide granular material.

Various procedures may be employed in order to apply and/or adsorb the desired active constituents and/or auxiliary substances on the silicon dioxide granular material. An exemplary process for the production of the adsorbate according to the invention comprises the following steps:

(a) melting of the substance(s) to be adsorbed, selected from pharmaceutical active constituents and auxiliary substances, or distribution, i.e. dissolution, suspension or emulsification, of the latter in a solvent;

(b) mixing the granular material based on pyrogenically produced silicon dioxide with the mixture from step (a); and (c) optionally removal of the solvent.

The term "solvent" also includes mixtures of several different solvents. It is also understood that substances already liquid at room temperature can be subjected without prior processing to the mixing in step (b) since in this case the "melting process" has already taken place. The mixing step (b) may be carried out either by adding the mixture from step (a) to the silicon dioxide granular material, for example by spraying, or vice versa. In both cases the addition may take place in one amount or in portions. The duration of the mixing in step (b) depends above all on the adsorption behaviour of the substance to be adsorbed on the silicic acid surface. If a solvent is present, step (a) and step (b) are carried out at a temperature that is between the freezing point and boiling point of the solvent. The excess solvent that may be present is removed in step (c), preferably at elevated temperature and/or reduced pressure.

The removal of the solvent in step (c) may also be effected by spray drying or fluidised bed drying, a forming being carried out at the same time. In the case of a melt containing granular material the forming process may appropriately comprise an extrusion.

Granular materials formed from pyrogenic silicic acids may however also be used for the production of pharmaceutical preparations without their simultaneously acting as carriers and/or adsorption agents. In this case they can in particular complement or replace the conventional pyrogenic silicic acids that have been established in pharmaceutical practice for many years. For example, granular materials of pyrogenic silicic acids may above all improve the production and properties of solid medicament forms. Also, they may advantageously be employed in the production of extrudates and replace for example other established auxiliary substances such as cellulose or polymers.

The advantages of the granular materials based on pyrogenically produced silicon dioxide compared to the known non-granulated pyrogenic silicic acids lie above all in the higher bulk density and tamped density, improved flowability, narrower grain size distribution, and dust-free processing. In addition tablets produced therefrom have a higher mechanical stability and an improved disintegration behaviour.

The invention will now be described in more detail with the aid of examples.

REFERENCE EXAMPLES A AND B

Production of the Granular Materials Based on Pyrogenically Produced Silicon Dioxide The pyrogenically produced silicon dioxides AEROSIL 90 and AEROSIL 300, both of which are commercially obtainable from Degussa AG, are used as starting compounds.

The pyrogenically produced silicon dioxide is dispersed in fully deionised water. In this connection dispersing equipment is used that operates according to the rotor/stator principle. The suspensions that are formed are spray dried. The deposition of the finished product is carried out using a filter or cyclone. The heat treatment of the spray-dried granular materials is carried out in muffle furnaces.

The production parameters are given in Table 1.

TABLE 1

| Reference Example | A | B |
|---|---|---|
| Starting SiO$_2$ | AEROSIL 90 | AEROSIL 300 |
| Data for the spray drying | | |
| Amount H$_2$O (kg) | 100 | 100 |
| Amount SiO$_2$ (kg) | 1.5 | 10 |
| Atomisation with | 1-substance nozzle | disc |
| operating temp. (° C.) | 358 | 380 |
| Exhaust air temp. (° C.) | 105 | 105 |
| Deposition | filter | filter |
| Physicochemical data | | |
| BET surface (m$^2$/g) | 87 | 279 |
| Grain size d$^{50}$ (μm) | 25 | 27.9 |
| Tamped volume (g/l) | 258 | 28.9 |
| pH value | 4.7 | 4.6 |
| Carbon content % | — | — |

EXAMPLES 1a AND 1b

SiO$_2$ Granular Materials Containing Vitamin E Acetate 50.0 g of the granular materials produced in reference examples A and B from AEROSIL 90 (Example 1a) and from AEROSIL 300 (Example 1b) were in each case placed in a tall 600 ml capacity beaker and 50.0 g of vitamin E acetate (from BASF) was stirred in in portions using a spatula. Both granular materials quickly absorbed the oily liquid, did not form any dust and did not produce an electrostatic charge.

The total amount of the vitamin E acetate could be processed within ten minutes. The dry mixtures were then screened through a sieve having a mesh width of 0.75 mm and allowed to stand overnight.

The flow score and shaking cone height were determined as described in the Technical Information Leaflet "Pigments" No. 31 "AEROSIL zur Verbesserung des Fließverhaltens pulverförmiger Substanzen" from Degussa AG. The bulk density and tamped density are according to DIN Norm 66131. The data are summarised in Table 2.

COMPARISON EXAMPLES 1a*-c*

Vitamin E Acetate on Non-granulated Pyrogenic SiO$_2$ (AEROSIL 90, 200 and 300, Degussa AG)

50.0 g of AEROSIL 90 (comparison example 1a*), AEROSIL 300 (comparison example 1b*) and AEROSIL 200 (comparison example 1c*) were placed in a tall 600 ml capacity beaker and 50.0 g of vitamin E acetate (BASF) were stirred in in portions using a spatula. The pyrogenic silicon dioxides absorbed the oily substance only very slowly, produced a large amount of dust and developed an electrostatic charge. A time of ca. two hours was needed to incorporate the total amount of vitamin E acetate. As in Example 1, the dry mixtures were then screened and allowed to stand overnight.

The flow score, shaking cone height, bulk and tamped densities were determined as in Example 1 and are also shown in Table 2.

TABLE 2

| | Examples | | Comparison Examples | | |
|---|---|---|---|---|---|
| | 1a | 1b | 1a* | 1b* | 1c* |
| Employed SiO$_2$ | AEROSIL 90 Granulate | AEROSIL 300 Granulate | AEROSIL 90 | AEROSIL 300 | AEROSIL 200 |
| Flow score | 1 | 1 | 5-6 | 5 | 4-5 |
| Shaking cone height (cm) | 1.35 | 1.20 | 3.00 | 2.90 | 4.50 |
| Bulk density (g/l) | 431 | 454 | 227 | 158 | 160 |
| Tamped density (g/l) | 500 | 568 | 290 | 215 | 222 |

The flow score and shaking cone height of the adsorbates on SiO$_2$ granular materials (Examples 1a and 1b) demonstrated a very good flow behaviour of both products. All three adsorbates of the comparison examples showed a poor flow behaviour. Also, the bulk and tamped densities were low and were not sufficient for many applications.

EXAMPLES 2a AND 2b

Hard Gelatin Capsules Containing Vitamin E Acetate (SiO$_2$ Granular Material)

Hard gelatin capsules of size 1 (Scherer, empty weight 71-78 mg) were filled with the vitamin E acetate adsorbates from Example 1 using a capsule-filling device (Simplex type, Raebiger). The mean capsule weights (mean value of 20 randomly selected capsules) are included together with the standard deviations of the weight in Table 3.

COMPARISON EXAMPLES 2a*-c*

Hard Gelatin Capsules Containing Vitamin E Acetate (Non-granulated SiO$_2$)

Hard gelatin capsules were filled as described in Example 2 with the vitamin E acetate adsorbates of comparison example 1*. The results are also shown in Table 3.

TABLE 3

| | Examples | | Comparison Examples | | |
|---|---|---|---|---|---|
| | 2a | 2b | 2a* | 2b* | 2c* |
| Employed SiO$_2$ | AEROSIL 90 Granulate | AEROSIL 300 Granulate | AEROSIL 90 | AEROSIL 300 | AEROSIL 200 |
| Capsule weight (mg) | 271 | 284 | 165 | 110 | 139 |
| Relative standard deviation (%) | 0.9 | 1.2 | 7.9 | 4.2 | 8.1 |

The capsules produced in Example 2 had a significantly higher weight that those of comparison example 2*, and therefore contained more active constituent. Also, in Example 2 the relative standard deviations of the capsule weight were substantially less than in comparison example 2*. The uniformity of the capsule weight is an important requirement of all Pharmacopoeias.

EXAMPLE 3

SiO₂ Granular Material Containing Acetylsalicylic Acid and Hard Gelatin Capsules Produced Therefrom 30 g of the granular material consisting of AEROSIL 300 produced in reference example B were added to a solution of 60 g of acetylsalicylic acid (Caelo) in 500 ml of acetone and the resultant mixture was stirred for two hours at room temperature with a magnetic stirrer. The acetone was then completely distilled off in a rotary evaporator at a water bath temperature of 40° C., and the resultant solid was dried for two hours at 45° C. in a drying cabinet and then allowed to stand overnight in a desiccator. The product was screened through a 0.75 mm sieve before the characterisation and further processing. Hard gelatin capsules were filled with the product according to the procedure of Example 2. The analytical data are summarised in Table 4.

COMPARISON EXAMPLE 3

Acetylsalicylic Acid on Non-granulated Pyrogenic SiO₂

Comparison example 3 was carried out similarly to Example 3. AEROSIL 300 was used instead of an AEROSIL 300 granular material. The analytical data are also shown in Table 4.

TABLE 4

|  | Example 3 | Comparison Example 3* |
|---|---|---|
| Employed SiO₂ | AEROSIL 300 Granulate | AEROSIL 300 |
| Shaking cone height (cm) | 1.6 | 1.7 |
| Bulk density (g/l) | 347 | 323 |
| Tamped density (g/l) | 454 | 410 |
| Mean capsule weight (mg) | 232 | 224 |
| Standard deviation of the capsule weight (%) | 1.65 | 2.6 |

The acetylsalicylic acid adsorbate (Example 3) produced with the AEROSIL 300 granular material has a better flowability as well as a higher bulk density and tamped density than the product (comparison example 3*) produced with AEROSIL 300. The mean capsule weight is also correspondingly higher in Example 3 than in comparison example 3*.

EXAMPLE 4

Acetylsalicylic Acid Tablets (SiO₂ Granular Material)

The product of Example 3 was used to produce tablets according to the formulation in Table 5.

TABLE 5

| Starting Substance | Commercial Name, Manufacturer | Amount per 600 mg Tablet (mg) | Content (wt. %) |
|---|---|---|---|
| Acetylsalicylic acid adsorbate | from Example 3 | 500.00 | 83.33 |
| Powdered cellulose | ELCEMA P 100 (Rettenmaier) | 62.2 | 10.4 |
| Corn starch | Corn starch | 30.00 | 5.00 |
| Stearic acid | (Caelo) Stearic acid (Merck) | 6.00 | 1.00 |
| Highly dispersed silicon dioxide | AEROSIL 200 (Degussa AG) | 1.8 | 0.3 |

To prepare a 200 g batch the powdered starting materials were weighed out in the specified sequence to an accuracy of 0.01 g and mixed by hand in a closed 1000 ml wide-necked glass flask. The mixture was screened through a sieve with a mesh width of 0.75 mm, readded to the already used glass flask, and homogenised with a Turbula mixer (Bachofen) for five minutes at an average speed setting (stage 3). The resultant powder mixture was characterised similarly to Example 1.

The mixture was then compressed into tablets using an eccentric press (EKO, Korsch, punch size 11 mm, flat punch with facets). The filling of the matrix and upper punch pressure of the press were adjusted so that tablets were formed having a weight of ca. 600 mg and a fracture hardness of ca. 100 N.

The tablets were characterised as follows:

Abrasion/friability: the rolling wear and falling wear of 10 tablets were measured with an abrasion tester (Erweka, Type TA 3) after 125 revolutions. The weight difference of the tablets before and after the test was measured.

Disintegration: the disintegration time of 6 tablets in water at 37° C. was determined using a disintegration tester (Erweka, Type ZT 31 on vibrating baskets).

The tablet hardness was measured in each case on 10 tablets with a semi-automatic hardness tester (Erweka, TBH 30 MD).

Mean tablet weight and standard deviation were determined in each case on 20 tablets using an analytical balance.

The analytical data are shown in Table 6.

COMPARISON EXAMPLE 4

Acetylsalicylic Acid Tablets (Non-granulated SiO₂)

Acetylsalicylic acid tablets were produced starting from the product of comparison example 3* similarly to Example 4 with the same machine setting, and characterised. The analytical data are given in Table 6.

TABLE 6

|  | Example 4 | Comparison Example 4* |
|---|---|---|
| Employed SiO₂ | AEROSIL 300 Granulate | AEROSIL 300 |
| Shaking cone (cm) | 1.8 | 1.9 |
| Bulk density (g/l) | 390 | 367 |
| Abrasion (%) | 1.0 | 1.3 |
| Disintegration (min) | <1 | 11 |
| Hardness (N) | 105 | 90 |
| Mean tablet weight (mg) | 604 | 532 |
| Standard deviation of the tablet weight (%) | 0.5 | 0.8 |

The powder mixture in Example 4 was more flowable compared to that in comparison example 4* and had a higher bulk density. The tablets of Example 4 were mechanically more stable than those of comparison example 4*, disintegrated more rapidly, and had a higher tablet weight as well as a smaller standard deviation of the weight.

EXAMPLE 5

Paracetamol Tablets (SiO₂ Granular Material)

Starting from the formulation in Table 7, Paracetamol tablets were produced similarly to Example 4 using an AEROSIL 300 granular material from reference example B. The analytical data are shown in Table 8.

TABLE 7

| Starting Substance | Amt. Weighed Out (g) | Concentration (wt. %) |
|---|---|---|
| Paracetamol | 166.60 | 83.3 |
| Microcrystalline cellulose (Unitab 101 F) | 25.60 | 12.8 |
| Corn starch | 6.00 | 3.0 |
| Magnesium stearate | 0.20 | 0.1 |
| AEROSIL 300 granulate | 1.60 | 0.8 |

COMPARISON EXAMPLE 5

Paracetamol Tablets (Non-granulated SiO₂)

Paracetamol tablets were produced similarly to Example 5 with non-granulated AEROSIL 300. The analytical data are likewise shown in Table 8.

TABLE 8

|  | Example 5 | Comparison Example 5* |
|---|---|---|
| Shaking cone height of the employed starting powder (cm) | 1.9 | 1.7 |
| Tablet abrasion (%) | 2.8 | 2.6 |
| Tablet disintegration (s) | 10 | <10 |
| Tablet hardness (N) | 63.6 | 65.6 |
| Tablet weight (mg) | 600.5 | 614.3 |

When using AEROSIL 300 granular material (Example 5) instead of non-granulated AEROSIL 300 (comparison example 5*), tablets were obtained having a higher mechanical stability, a more rapid disintegration, and a higher tablet weight. In addition the powder mixture used for the tabletting was more flowable (smaller shaking cone height).

The invention claimed is:

1. A pharmaceutical composition comprising granular pyrogenically produced silicon dioxide, having void volumes, and at least one pharmaceutical active constituent, wherein the granular silicon dioxide has meso- and macropores, a mean grain diameter of 10 to 120 μm and a BET surface of 40 to 400 m²/g, determination according to DIN 66 131 using nitrogen, wherein the mesopores account for 10 to 80% of the total volume and the particle size distribution of the granular material is 80 vol. % greater than 8 μm and 80% less than 96 μm and the proportion of the pores less than 5 μm be at most 5% referred to the total pore volume.

2. The pharmaceutical composition according to claim 1 further comprising at least one pharmaceutical auxiliary substance.

3. The pharmaceutical composition according to claim 1, wherein the pharmaceutical active constituent is selected from:

α-proteinase inhibitor, abacavir, abciximab, acarbose, acetylsalicylic acid, acyclovir, adenosine, albuterol, aldesleukin, alendronate, alfuzosin, alosetrone, alprazolam, alteplase, ambroxol, amifostine, amiodarone, amisulprid, amlodipine, amoxicillin, amphetamine, amphotericin, ampicillin, amprenavir, anagrelide, anastrozole, ancrod, anti-haemophilia factor, aprotinin, atenolol, atorvastatin, atropine, azelastine, azithromycin, azulene, barnidipin, beclomethasone, benazepril, benserazide, beraprost, betamethasone, betaxolol, bezafibrate, bicalutamide, bisabolol, bisoprolol, botulinum toxin, brimonidine, bromazepam, bromocriptine, budesonide, bupivacaine, bupropion, buspirone, butorphanol, cabergoline, calcipotriene, calcitonin, calcitriol, camphor, candesartan, candesartan cilexetil, captopril, carbamazepine, carbidopa, carboplatin, carvedilol, cefaclor, cefadroxil, cefaxitin, cefazolin, cefdinir, cefepime, cefixime, cefmetazole, cefoperazone, cefotiam, cefoxopran, cefpodoxime, cefprozil, ceftazidime, ceftibuten, ceftriaxone, cefuroxime, celecoxib, celiprolol, cephalexin, cerivastatin, cetirizine, chloramphenicol, cilastatin, cilazapril, cimetidine, ciprofibrate, ciprofloxacin, cisapride, cisplatin, citalopram, clarithromycin, clavulanic acid, clindamycin, clomipramine, clonazepam, clonidine, clopidogrel, clotrimazole, clozapine, cromolyn, cyclophosphamide, cyclosporine, cyproterone, dalteparin, deferoxamine, desogestrel, dextroamphetamine, diazepam, diclofenac, didanosine, digitoxin, digoxin, dihydroergotamine, diltiazem, diphtheria protein, diphtheria toxoxide, divalproex, dobutamine, docetaxel, dolasetron, donepezil, dornase-α, dorzolamide, doxazosin, doxifluridin, doxorubicin, dydrogesterone, ecabet, efavirenz, enalapril, enoxaparin, eperisone, epinastin, epirubicin, eptifibatide, erythropoietin-α, erythropoietin-β, etanercept, ethinyl oestradiol, etodolac, etoposide, factor VIII, famciclovir, famotidine, faropeneme, felodipine, fenofibrate, fenoldopam, fentanyl, fexofenadin, filgrastim, finasteride, flomoxef, fluconazole, fludarabine, flunisolide, flunitrazepam, fluoxetine, flutamide, fluticasone, fluvastatin, fluvoxamine, follitropin-α, follitropin-β, formoterol, fosinopril, furosemide, gabapentin, gadodiamide, ganciclovir, gatifloxacin, gemcitabine, gestoden, glatiramer, glibenclamide, glimepiride, glipizide, glyburide, goserelin, granisetron, griseofulvin, hepatitis B antigen, hyaluronic acid, hycosin, hydrochlorothiazide, hydrocodone, hydrocortisone, hydromorphone, hydroxychloroquine, hylan G-F 20, ibuprofen, ifosfamide, imidapril, imiglucerase, imipenem, immunoglobulin, indinavir, indomethacin, infliximab, insulin, insulin human, insulin Lispro, insulin aspart, interferon β, interferon α, iodine 125, iodixanol, iohexol, iomeprol, iopromid, ioversol, ioxoprolen, ipratropium, ipriflavone, irbesartan, irinotecan, isosorbide, isotretinoin, isradipine, itraconazole, potassium chlorazepate, potassium chloride, ketorolac, ketotifen, whooping cough vaccine, coagulation factor IX, lamivudine, lamotrigine, lansoprazole, latanoprost, leflunomide, lenograstim, letrozole, leuprolide, levodopa, levofloxacin, levonorgestrel, levothyroxine, lidocaine, linezolid, lisinopril, lopamidol, loracarbef, loratadine, lorazepam, losartan, lovastatin, lysineacetylsalicylic acid, manidipin, mecobalamin, medroxyprogesterone, megestrol, meloxicam, menatetrenone, meningococcus vaccine, menotropine, meropenem, mesalamine, metaxalone, metformin, methylphenidate, methylprednisolone, metoprolol, midazolam, milrinone, minocycline, mirtazapine, misoprostol, mitoxantrone, moclobemid, modafinil, mometasone, montelukast, morniflumat, morphine, moxifloxacin, mycophenolate, nabumetone, nadroparin, naproxen, naratriptan, nefazodone, nelfinavir, nevirapine, niacin, nicardipine, nicergoline, nifedipine, nilutamide, nilvadipine, nimodipine, nitroglycerin, nizatidine, norethindrone, norfloxacin, octreotide, olanzapine, omeprazole, ondansetron, orlistate, oseltamivir, oestradiol, oestrogens, oxaliplatin, oxaprozin, oxolinic acid, oxybutynin, paclitaxel, palivizumab, pamidronate, pancrelipase, panipenem, pantoprazol, paracetamol, paroxetine, pentoxifylline, pergolide, phenytoin, pioglitazon, piperacillin, piroxicam, pramipexole, pravastatin, prazosin, probucol, progesterone, propafenone, propofol, propoxyphene, prostaglandin, quetiapine, quinapril, rabeprazol, raloxifene, ramipril, ranitidine, repaglinide, reserpine, ribavirin, riluzole, risperidone, ritonavir, rituximab, rivastigmin, rizatriptan, rofecoxib, ropinirol, rosiglitazone, salmeterol, saquinavir, sargramostim, serrapeptase, sertraline, sevelamer, sibutramin, sildenafil, simvastatin, somatropine, sotalol, spironolactone, stavudin, sulbactam, sulfaethidole, sulfamethoxazole, sulfasalazin, sulpirid, sumatriptan, tacrolimus, tamoxifen, tamsulosin, tazobactam, teicoplanin, temocapril, temozolomid, tenecteplase, tenoxicam, teprenon, terazosin, terbinafine, terbutaline, tetanus toxoid, tetrabenazine, tetrazepam, thymol, tiagabine, tibolon, ticarcillin, ticlopidine, timolol, tirofiban, tizanidine, tobramycin, tocopheryl nicotinate, tolterodine, topiramate, topotecan, torasemid, tramadol, trandolapril, trastuzumab, triamcinolone, triazolam, trimebutin, trimethoprim, troglitazone, tropisetrone, tulobuterol, unoproston, urofollitropine, valaciclovir, valproic acid, valsartan, vancomycin, venlafaxine, verapamil, verteporfin, vigabatrin, vinorelbine, vinpocetine, voglibose, warfarin, zafirlukast, zaleplon, zanamivir, zidovudine, zolmitriptan, zolpidem, zopiclone or their derivatives.

4. The pharmaceutical composition according to claim 2, wherein the pharmaceutical auxiliary substance is selected from:
antioxidants, binders, emulsifiers, colouring agents, film-forming agents, fillers, gel-forming agents, odoriferous substances, flavouring substances, preservatives, solvents, oils, powder bases, ointment bases, acids and salts for the formulation, replenishment and production of pharmaceutical compositions, lubricants, release agents, suppository bases, suspension stabilisers, sweetening agents, effervescent gases, emollients or sugar substitutes.

5. An adsorbate comprising granular pyrogenically produced silicon dioxide, having void volumes, and absorbed on a surface and/or incorporated within the void volumes, at least one further substance selected from pharmaceutical active constituents and auxiliary substances, wherein the granular silicon dioxide has meso- and macropores, a mean grain diameter of 10 to 120 μm and a BET surface of 40 to 400 m²/g, determination according to DIN 66 131 using nitrogen and the mesopores account for 10 to 80% of the total volume and the particle size distribution of the granular material is 80 vol. % greater than 8 μm and 80% less than 96 μm and the proportion of the pores less than 5 μm be at most 5% referred to the total pore volume, and wherein the adsorbate is prepared by forming a mixture by melting the substance(s) to be adsorbed, selected from pharmaceutical active constituents and auxiliary substances, or dissolving or dispersing the substance in a solvent; adsorbing the substance(s) by mixing the granular pyrogenically produced silicon dioxide with the mixture; and removing the solvent, when present.

6. The adsorbate according to claim 5, wherein the pharmaceutical active constituent is selected from:
α-proteinase inhibitor, abacavir, abciximab, acarbose, acetylsalicylic acid, acyclovir, adenosine, albuterol, aldesleukin, alendronate, alfuzosin, alosetrone, alprazolam, alteplase, ambroxol, amifostine, amiodarone, amisulprid, amlodipine, amoxicillin, amphetamine, amphotericin, ampicillin, amprenavir, anagrelide, anastrozole, ancrod, anti-haemophilia factor, aprotinin, atenolol, atorvastatin, atropine, azelastine, azithromycin, azulene, barnidipin, beclomethasone, benazepril, benserazide, beraprost, betamethasone, betaxolol, bezafibrate, bicalutamide, bisabolol, bisoprolol, botulinum toxin, brimonidine, bromazepam, bromocriptine, budesonide, bupivacaine, bupropion, buspirone, butorphanol, cabergoline, calcipotriene, calcitonin, calcitriol, camphor, candesartan, candesartan cilexetil, captopril, carbamazepine, carbidopa, carboplatin, carvedilol, cefaclor, cefadroxil, cefaxitin, cefazolin, cefdinir, cefepime, cefixime, cefmetazole, cefoperazone, cefotiam, cefoxopran, cefpodoxime, cefprozil, ceftazidime, ceftibuten, ceftriaxone, cefuroxime, celecoxib, celiprolol, cephalexin, cerivastatin, cetirizine, chloramphenicol, cilastatin, cilazapril, cimetidine, ciprofibrate, ciprofloxacin, cisapride, cisplatin, citalopram, clarithromycin, clavulanic acid, clindamycin, clomipramine, clonazepam, clonidine, clopidogrel, clotrimazole, clozapine, cromolyn, cyclophosphamide, cyclosporine, cyproterone, dalteparin, deferoxamine, desogestrel, dextroamphetamine, diazepam, diclofenac, didanosine, digitoxin, digoxin, dihydroergotamine, diltiazem, diphtheria protein, diphtheria toxoxide, divalproex, dobutamine, docetaxel, dolasetron, donepezil, dornase-a, dorzolamide, doxazosin, doxifluridin, doxorubicin, dydrogesterone, ecabet, efavirenz, enalapril, enoxaparin, eperisone, epinastin, epirubicin, eptifibatide, erythropoietin-α, erythropoietin-β, etanercept, ethinyl oestradiol, etodolac, etoposide, factor VIII, famciclovir, famotidine, faropeneme, felodipine, fenofibrate, fenoldopam, fentanyl, fexofenadin, filgrastim, finasteride, flomoxef, fluconazole, fludarabine, flunisolide, flunitrazepam, fluoxetine, flutamide, fluticasone, fluvastatin, fluvoxamine, follitropin-α, follitropin-β, formoterol, fosinopril, furosemide, gabapentin, gadodiamide, ganciclovir, gatifloxacin, gemcitabine, gestoden, glatiramer, glibenclamide, glimepiride, glipizide, glyburide, goserelin, granisetron, griseofulvin, hepatitis B antigen, hyaluronic acid, hycosin, hydrochlorothiazide, hydrocodone, hydrocortisone, hydromorphone, hydroxychloroquine, hylan G-F 20, ibuprofen, ifosfamide, imidapril, imiglucerase, imipenem, immunoglobulin, indinavir, indomethacin, infliximab, insulin, insulin human, insulin Lispro, insulin aspart, interferon β, interferon α, iodine 125, iodixanol, iohexol, iomeprol, iopromid, ioversol, ioxoprolen, ipratropium, ipriflavone, irbesartan, irinotecan, isosorbide, isotretinoin, isradipine, itraconazole, potassium chlorazepate, potassium chloride, ketorolac, ketotifen, whooping cough vaccine, coagulation factor IX, lamivudine, lamotrigine, lansoprazole, latanoprost, leflunomide, lenograstim, letrozole, leuprolide, levodopa, levofloxacin, levonorgestrel, levothyroxine, lidocaine, linezolid, lisinopril, lopamidol, loracarbef, loratadine, lorazepam, losartan, lovastatin, lysineacetylsalicylic acid, manidipin, mecobalamin, medroxyprogesterone, megestrol, meloxicam, menatetrenone, meningococcus vaccine, menotropine, meropenem, mesalamine, metaxalone, metformin, methylphenidate, methylprednisolone, metoprolol, midazolam, milrinone, minocycline, mirtazapine, misoprostol, mitoxantrone, moclobemid, modafinil, mometasone, montelukast, morniflumat, morphine, moxifloxacin, mycophenolate, nabumetone, nadroparin, naproxen, naratriptan, nefazodone, nelfinavir, nevirapine, niacin, nicardipine, nicergoline, nifedipine, nilutamide, nilvadipine, nimodipine, nitroglycerin, nizatidine, norethindrone, norfloxacin, octreotide, olanzapine, omeprazole, ondansetron, orlistate, oseltamivir, oestradiol, oestrogens, oxaliplatin, oxaprozin, oxolinic acid, oxybutynin, paclitaxel, palivizumab, pamidronate, pancrelipase, panipenem, pantoprazol, paracetamol, paroxetine, pentoxifylline, pergolide, phenytoin, pioglitazon, piperacillin, piroxicam, pramipexole, pravastatin, prazosin, probucol, progesterone, propafenone, propofol, propoxyphene, prostaglandin, quetiapine, quinapril, rabeprazol, raloxifene, ramipril, ranitidine, repaglinide, reserpine, ribavirin, riluzole, risperidone, ritonavir, rituximab, rivastigmin, rizatriptan, rofecoxib, ropinirol, rosiglitazone, salmeterol, saquinavir, sargramostim, serrapeptase, sertraline, sevelamer, sibutramin, sildenafil, simvastatin, somatropine, sotalol, spironolactone, stavudin, sulbactam, sulfaethidole, sulfamethoxazole, sulfasalazin, sulpirid, sumatriptan, tacrolimus, tamoxifen, tamsulosin, tazobactam, teicoplanin, temocapril, temozolomid, tenecteplase, tenoxicam, teprenon, terazosin, terbinafine, terbutaline, tetanus toxoid, tetrabenazine, tetrazepam, thymol, tiagabine, tibolon, ticarcillin, ticlopidine, timolol, tirofiban, tizanidine, tobramycin, tocopheryl nicotinate, tolterodine, topiramate, topotecan, torasemid, tramadol, trandolapril, trastuzumab, triamci- nolone, triazolam, trimebutin, trimethoprim, troglitazone, tropisetrone, tulobuterol, unoproston, urofollitropine, valaciclovir, valproic acid, valsartan, vancomycin, venlafaxine, verapamil, verteporfin, vigabatrin, vinorelbine, vinpocetine, voglibose, warfarin, zafirlukast, zaleplon, zanamivir, zidovudine, zolmitriptan, zolpidem, zopiclone or their derivatives.

7. The adsorbate according to claim 5, wherein the pharmaceutical auxiliary substance is selected from:
antioxidants, binders, emulsifiers, colouring agents, film-forming agents, fillers, gel-forming agents, odoriferous substances, flavouring substances, preservatives, solvents, oils, powder bases, ointment bases, acids and salts for the formulation, replenishment and production of pharmaceutical compositions, lubricants, release agents, suppository bases, suspension stabilisers, sweetening agents, effervescent gases, emollients or sugar substitutes.

8. Process for the production of an adsorbate, comprising the following steps:
(a) forming a mixture by melting the substance(s) to be adsorbed, selected from pharmaceutical active constituents and auxiliary substances, or by dissolving or dispersing the substance(s) in a solvent;
(b) adsorbing the substance(s) by mixing the granular pyrogenically produced silicon dioxide, having meso and macro pores, a mean grain diameter of 10 to 120 μm and a BET surface of 40 to 400 $m^2/g$, determination according to DIN 66 131 using nitrogen, and the mesopores account for 10 to 80% of the total volume and the particle size distribution of the granular material is 80 vol. % greater than 8 pm and 80% less than 96 μm and the proportion of the pores less than 5 μm be at most 5% referred to the total pore volume, with the mixture from step (a) under conditions where no dust or electrostatic charge is formed; and
(c) removing the solvent, when present.

\* \* \* \* \*